(12) United States Patent
Fleischmann

(10) Patent No.: US 6,555,729 B1
(45) Date of Patent: Apr. 29, 2003

(54) PROCESS AND BANDAGE FOR TREATMENT OF WOUNDS

(76) Inventor: Wilhelm Fleischmann, Wieselweg 26, D-74321 Bietighelm-Bissingen (DE)

( * ) Notice: Subject to any disclaimer, the term of this patent is extended or adjusted under 35 U.S.C. 154(b) by 0 days.

(21) Appl. No.: 09/915,106

(22) Filed: Jul. 25, 2001

Related U.S. Application Data

(63) Continuation of application No. 09/484,116, filed on Jan. 14, 2000.

(30) Foreign Application Priority Data

Jan. 14, 1999 (DE) ......................................... 199 01 134

(51) Int. Cl.[7] .................................................. A61F 13/00
(52) U.S. Cl. ............................ 602/41; 602/42; 602/43; 602/44; 602/45; 602/46; 602/47
(58) Field of Search ..................................... 602/41–47

(56) References Cited

U.S. PATENT DOCUMENTS

| | | |
|---|---|---|
| 4,668,228 A | 5/1987 | Bolton et al. |
| 4,904,469 A | 2/1990 | Petereit et al. |

FOREIGN PATENT DOCUMENTS

| | | | |
|---|---|---|---|
| DE | 31 39 089 A1 | 4/1983 | ............. A61K/9/70 |
| EP | 0 236 610 | 9/1987 | ............. A61L/15/03 |
| EP | 0 194 647 B1 | 11/1989 | ............. A61L/15/06 |

OTHER PUBLICATIONS

Sherman R A "Maggot Therapy—The Last Five Years" European Tissue Repair Society Bulletin, vol. 7, No. 3, 2001 (available at http://64.33.115.36/bulletin7_3/section12.html).

Thomas S et al.: "Maggots in wound debreidement—an introduction", last modified Mar. 22, 1999, available at http://www.smtl.co.uk/WMPRC/Maggots/maggots.htm.

Internet publication at http://www.smtl.co.uk/WMPRC/DataCards/HTML/larvae.html.

Hall, M.: "Introduction to Myiasis: The Entomological Origins of Larva Therapy", Abstracts from the 1st World Conference on Biosurgery Internet published 1996 at http://www.smtl.co.uk/WMPRC/BioSurgery/Conference/abstracts96.html.

Marxer N: "Fliegenmade als Saubermann für die Wunde", GOVI Verlag, 1999 (in German).

Sherman R A: "A new dressing design for use with maggot therapy", Plastic and reconstructive Surgery, vol. 100, 1997, pp. 451–456.

Prete P E: "Growth effects of Phaenicia sericata larval extracts on fibroblasts: Mechanisms for wound healing by maggot therapy", Life Sciences, vol. 60, No. 8, 1997, pp. 505–510.

Fine A et al.: "Maggot therapy. Technique and Clinical Application", Journal of Bone and Joint Surgery, vol. 16A, 1934, pp. 572–582.

*Primary Examiner*—Nicholas D. Lucchesi
*Assistant Examiner*—Lalita M Hamilton
(74) *Attorney, Agent, or Firm*—Pendorf & Cutlift

(57) ABSTRACT

A bandage for treatment of wounds is described, including a wound overlay, which contains the secretion of fly larvae. The wound overlay can be a single pouch or may be subdivided into chambers, which enclose living fly larvae. It is likewise possible to soak or permeate the wound overlay with the secretion of fly larvae.

3 Claims, 1 Drawing Sheet

PROCESS AND BANDAGE FOR TREATMENT OF WOUNDS

REFERENCE TO RELATED APPLICATION

This application is a continuation of application Ser. No. 09/484,116 filed Jan. 14, 2000.

BACKGROUND OF THE INVENTION

1. Field of the Invention

The invention concerns a process and a bandage for treatment of wounds.

For treatment of wound infections and wounds which contain dead tissue, for example, for treatment of the diabetic gangrene, fly larvae are employed, in particular larvae of the fly genus Lucilia (bluebottle flies) and in particular *Lucilia scricata*. The fly larvae (maggots) are employed for a specific amount of time, for example three days, in the wound in need of therapy. It has been shown that the maggots in this time remove necrotic tissue in the wound (biodebridement), eliminate bacterial infections and stimulate healing of the wound.

2. Description of the Related Art

In the method for treatment with surgical maggots employed until now, after cleansing of the wound the edge or rim of the wound is first covered with an adhesive strip. The maggots are applied to a fine mesh net, which is then inverted and adhered to the adhesive strips, such that the maggots are situated between the net and the wound surface. The net serves as an air-permeable cage, which restrains the maggots in the wound. After the effective time of approximately three days, the net is pulled off and the maggots are removed from the wound.

In this method, various problems can occur. The adhesive bond between the net and the wound edge is not absolutely reliable. If the adhesive edge comes loose, it is not possible to prevent escape of maggots, which can then pupate so that bottle flies develop. The removal of the maggots from the wound after conclusion of the treatment is time-consuming and, in particular for the patients, is not aesthetic. Further, in larger wounds it cannot be guaranteed that the maggots are active in particular there where the strongest therapeutic effect is to be targeted.

SUMMARY OF THE INVENTION

The present invention is concerned with a task of providing a process and a bandage for treatment of wounds, which overcome or reduce the above-mentioned disadvantages associated with the known treatment with surgical maggots.

The invention is based upon the recognition that the therapeutic effect of the maggots on the wound is in particular attributable to the secretions secreted by the maggots. These secretions, in particular the digestive secretions, liquefy necrotic tissue so that it can be taken up by the maggots as nutrient. The secreted fluid has a strongly anti-bacterial effect and promotes wound healing.

The fundamental concept of the invention is based on the idea that the maggots are not to be freely released into the wound, system. By means of such a ventilation system sufficient air can be introduced under the foil and into the open-pore insert, in order to ensure the survival of the maggots. In order to prevent the escape through the ventilation system of the odors evolved in the wound, the ventilation system is preferably closeable or sealable. When air is being supplied below the air-tight covering, the ventilation system is opened and the flow-through of air is carried out through the open porous insert. The emitted odors can, as desired, be captured by an odor filter. Between the individual ventilation phases, the ventilation system can be closed by an air-tight lid.

BRIEF DESCRIPTION OF THE DRAWINGS

In the following the invention will be described in greater detail by reference to the attached drawings. There is shown.

DETAILED DESCRIPTION OF THE INVENTION

Figure 1:
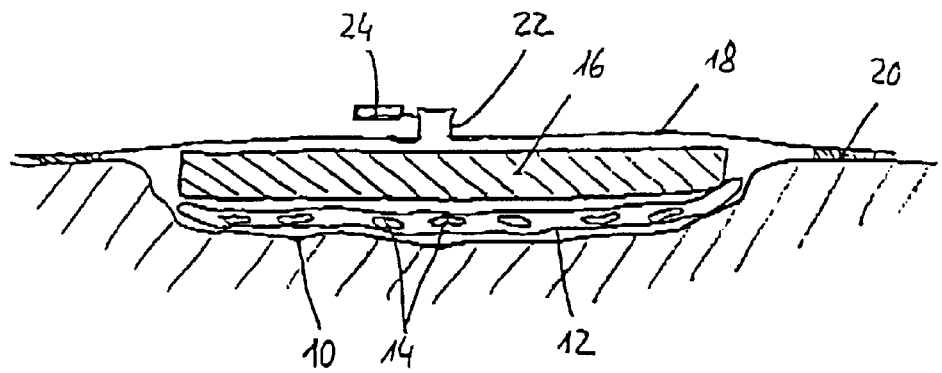
FIG. 1 a vertical section through a wound with bandage.

The pouch 12 comprised of a fine-mesh net-like material is introduced in a wound 10. The sheet-like pouch 12 is closed around its edges. In the pouch 12 there are enclosed sterile-bred living maggots 14 of the fly species *Lucilia sericata*. On the pouch 12 there is applied an insert 16 cut to conform to the wound surface, which insert is comprised of an open-pore foam plastic. The entire wound 10 including the wound overlay formed by the pouch 12 and the open-pore insert 16 is covered over by an air impermeable foil 18, which is securely adhered around the edges of the wound 10 in an air-tight manner using an adhesive substance 20. The foil 18 serving as wound covering includes for ventilation a connector 22, which can be closed off by means of a cap 24 connected to the connector 22 via a flexible flat connector.

For ventilation of the open-pore insert 16 a ventilation system, which may include an odor filter, is connected to the connector 22. Between the individual ventilations, the connector 22 is closed off air tight by means of the cap 24. In a simple manner, the ventilation can also be carried out manually by raising and compressing the foil 18.

Figure 2:
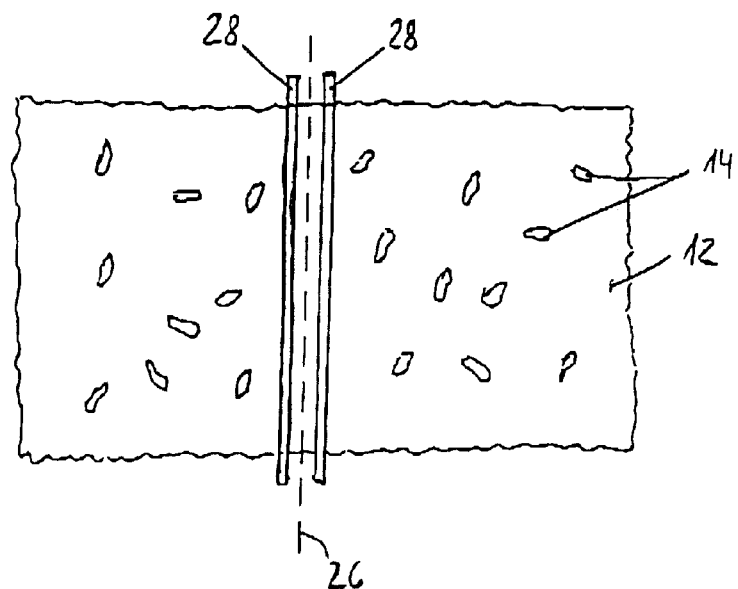
FIG. 2 a fly-larvae enclosing pouch.

Preferably the wound overlay is provided in the form of a large surface area pouch 12. This pouch 12 can as required be subdivided into smaller pouches. As shown in FIG. 2, for this the pouch is closed off on both sides by a desired separation line 26, for which for example plastic clamps 28 can be employed. Likewise an adhering of the two pouch edges is possible. After the closing off of the pouch by the clamps 28 or as the case may be an adhesive, the pouch 12 can be cut through along the separation line 26, so that two closed partial pouches are obtained.

In place of a pouch 12 containing living maggots 14, it is also possible to employ a wound overlay, which is made of a material impregnated with the secretion of fly larvae 14.

Figure 3:
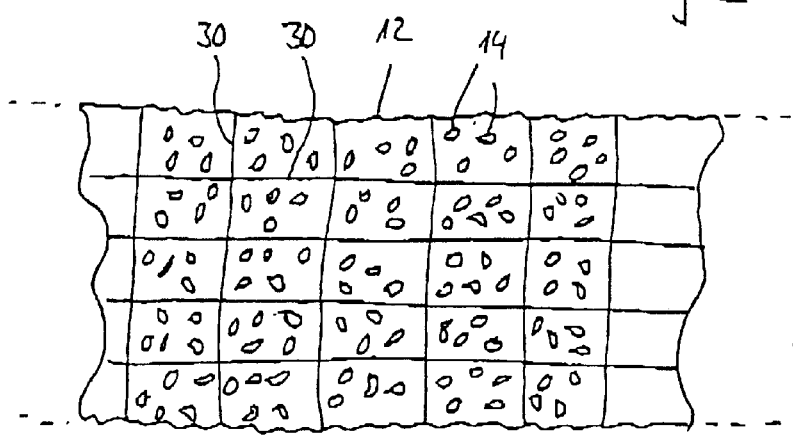
FIG. 3 a pouch subdivided into chambers in a grid-like manner.

In FIG. 3 a further embodiment of the wound overlay is shown. The pouch 12 is comprised of a two-layer sheet of the fine-mesh net-like textile material. Adhesive weld lines or beads 30

What is claimed is:

1. A bandage for treatment of wounds, comprising;

living fly larvae, and a pouch (12) of a fine-mesh net material enclosing said fly larvae (14), wherein said fine-mesh material has a pore size allowing a fluid exchange of secretions of fly larvae and dissolved necrotic tissue from said wound, and is dimensioned to retain said larvae in said pouch and to separate said fly larvae from said wound, said bandage further including at least one of a wound cover covering the pouch (12) and an insert (16), wherein the wound covering is an air-impermeable foil (18).

2. A bandage according to claim 1, wherein the wound cover (18) includes an adhesive material (20) for adhesion to the wound edge.

3. A bandage according to claim 1, wherein the air impermeable wound covering (18) includes a closeable ventilation access (22, 24).

* * * * *